US008019444B2

(12) United States Patent
Zarembo

(10) Patent No.: US 8,019,444 B2
(45) **Date of Patent: *Sep. 13, 2011**

(54) LEAD INTERCONNECT USING A CAPTURED FIXATION MEMBER

(75) Inventor: Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/019,878

(22) Filed: Feb. 2, 2011

(65) Prior Publication Data

US 2011/0125239 A1 May 26, 2011

Related U.S. Application Data

(63) Continuation of application No. 12/478,398, filed on Jun. 4, 2009, now Pat. No. 7,904,177.

(60) Provisional application No. 61/075,347, filed on Jun. 25, 2008.

(51) Int. Cl.
*A61N 1/00* (2006.01)

(52) U.S. Cl. ........................................ 607/121

(58) Field of Classification Search .................. 607/121, 607/122
See application file for complete search history.

(56) References Cited

U.S. PATENT DOCUMENTS

| | | | | |
|---|---|---|---|---|
| 4,214,804 | A * | 7/1980 | Little | 439/502 |
| 4,452,254 | A | 6/1984 | Goldberg et al. | |
| 5,488,768 | A | 2/1996 | Mar | |
| 6,564,107 | B1 * | 5/2003 | Bodner et al. | 607/122 |
| 6,687,550 | B1 | 2/2004 | Doan | |
| 6,901,289 | B2 | 5/2005 | Dahl et al. | |
| 7,003,351 | B2 | 2/2006 | Tvaska et al. | |
| 7,158,837 | B2 | 1/2007 | Osypka et al. | |
| 2002/0111664 | A1 | 8/2002 | Bartig et al. | |
| 2003/0060868 | A1 | 3/2003 | Janke et al. | |

* cited by examiner

*Primary Examiner* — George Manuel
*Assistant Examiner* — Robert N Wieland
(74) *Attorney, Agent, or Firm* — Faegre & Benson LLP

(57) ABSTRACT

Methods and devices for interconnecting a medical lead conductor member and an electrode are provided. One device includes a medical lead having a shaft. The shaft has a conductor member extending therethrough and a ring electrode disposed along the shaft. The ring electrode has a fixation device disposed within the ring electrode, and the fixation device forms an interference fit with the conductor member, forming an electrical contact therebetween. Also provided are methods for forming an electrical interconnect between a ring electrode and a conductor member.

20 Claims, 7 Drawing Sheets

10 12 18 14 16 1 22 20 24 26

LEAD INTERCONNECT USING A CAPTURED FIXATION MEMBER

CROSS-REFERENCE TO RELATED APPLICATIONS

This application is a continuation of U.S. application Ser. No. 12/478,398, filed Jun. 4, 2009, now U.S. Pat. No. 7,904,177 which claims the benefit under 35 U.S.C.§119(e) to U.S. Provisional Patent Application No. 61/075,347, filed Jun. 25, 2008, entitled "Lead Interconnect Using a Captured Fixation Member," both are incorporated herein by reference in their entirety.

BACKGROUND

Medical leads are used in many medical procedures to communicate electrical signals to or from a portion of a patient's body. For example, cardiac leads are used to pace or shock a patient's heart and/or to sense the electrical signals in a patient's heart. In other applications, neurological leads are used to stimulate a portion of a patient's nervous system and/or to sense electrical activity in a portion of a patient's nervous system. There is a need for alternative designs and methods of construction for medical leads.

SUMMARY

In one embodiment of the present invention, a medical lead comprises an elongate lead body including a coil conductor extending from a proximal portion of the lead body to a distal portion of the lead body. A ring electrode is disposed along the coil conductor and includes an outer electrically active surface and the ring electrode defines an inner cavity with a fixation member disposed therein. The fixation member is captured within the cavity and the fixation member exerts a compressive force on the coil conductor, mechanically and electrically connecting the coil conductor to the fixation member and the ring electrode. Further, an outer surface of the ring electrode is treated to provide a coated and/or textured surface.

In another embodiment of the present invention, a medical lead comprises an elongate shaft including a conductor member extending from a proximal portion of the shaft to a distal portion of the shaft. An electrode is disposed along the shaft and the electrode includes a ring member and a fixation member captured within the ring member. The fixation member forms an interference fit with the conductor member, forming an electrical connection between the fixation member and the conductor member.

In yet another embodiment of the present invention, a method of making a medical lead comprises providing a coil conductor and providing an electrode having a ring member and a fixation member disposed within the ring member, the fixation member sized and configured to form an interference fit with the coil conductor. The method further comprises disposing the electrode over a portion of the coil conductor, forming an interference fit between the fixation member and the coil conductor and disposing an insulative material over the coil conductor distal and proximal of the electrode.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
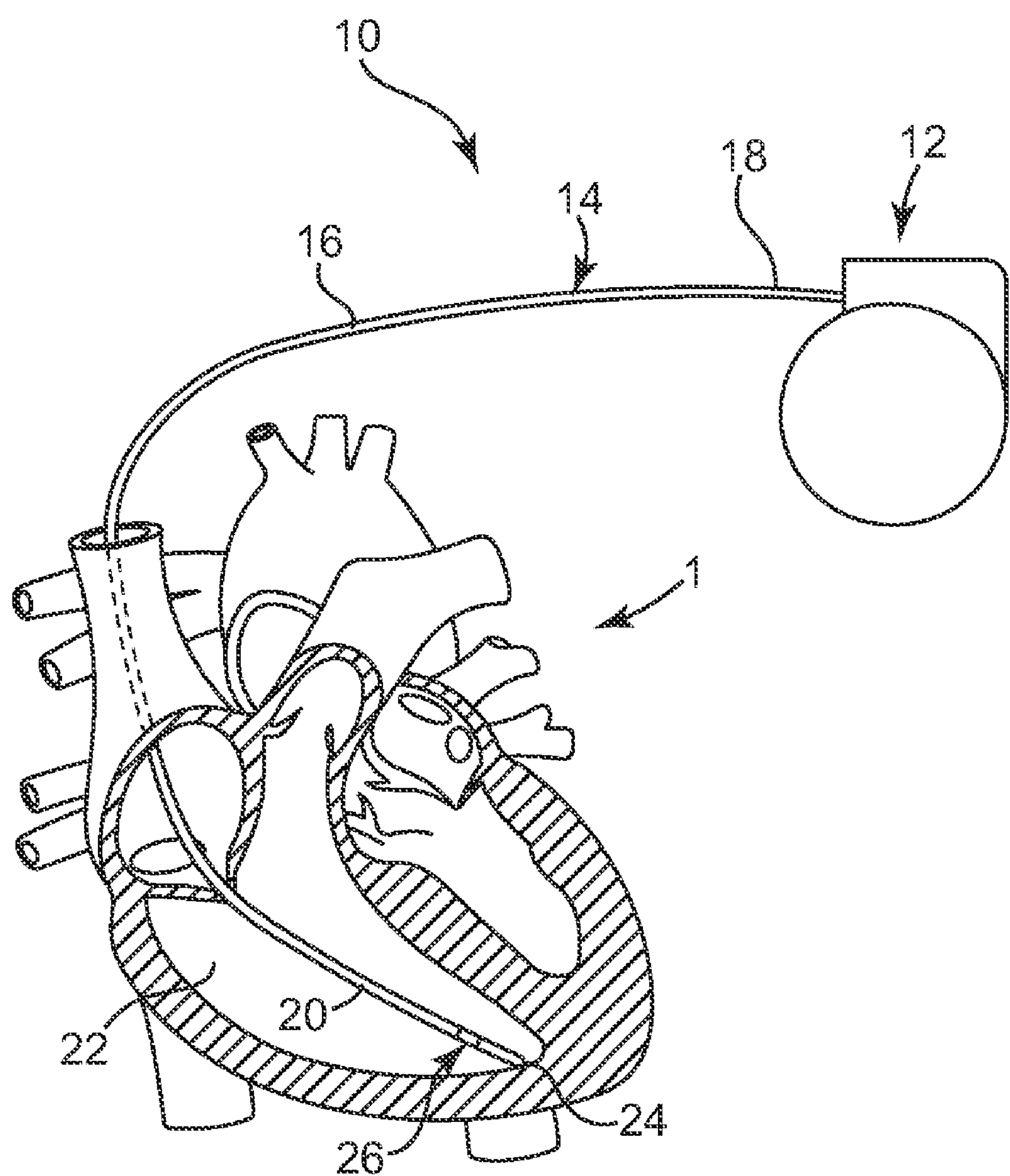
FIG. 1 shows a cut-away view of a human heart together with a cardiac pacing system according to some embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a cut-away view of a human heart 1 together with a cardiac pacing system 10 according to some embodiments of the present invention. The cardiac pacing system 10 has a pulse generator 12 and a lead 14 attached to the pulse generator 12. The lead 14 has a shaft 16 with a proximal portion 18 and a distal portion 20. The distal portion 20 extends through a patient's vasculature and into the right ventricle 22 of the heart 1. A distal end 24 of the lead 14 is optionally implanted at a location in the right ventricle 22, for example near the apex of the heart 1. Further, the lead 14 includes a ring electrode 26 disposed along the shaft 16 adjacent the shaft distal end 24.

Figure 2:
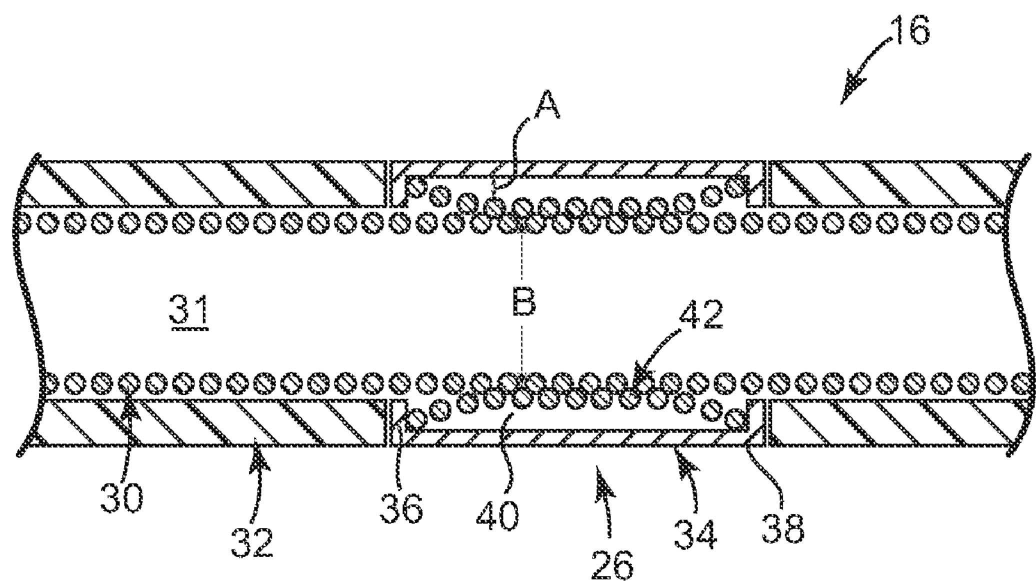
FIG. 2 shows a longitudinal cross-section of a portion of a medical lead according to some embodiments of the present invention.

FIG. 2 shows a longitudinal cross-section of a portion of the lead shaft 16 according to some embodiments of the present invention. The lead shaft 16 includes a conductor member 30 which extends from a proximal portion to a distal portion of the lead shaft 16 and defines a lumen 31. As shown, the conductor member 30 is a coil conductor. In other embodiments, the conductor member 30 is a braided conductor or, as shown below in FIGS. 9A-10B, a cable conductor, or any other suitable structure. As shown in FIG. 2, an insulative member 32 is disposed over at least a portion of the conductor member 30.

The electrode 26 is disposed along a portion of the lead shaft 16. The electrode 26 has a ring or containment member 34. In some embodiments, the ring 34 has a proximal flange 36 and a distal flange 38. Together, the ring 34 and the proximal and distal flanges 36, 38 form a cavity 40. Disposed within the cavity 40 is a fixation member 42. The fixation member 42 forms an interference fit with the conductor member 30 in order to provide for electrical and mechanical engagement between the electrode 26 and the conductor member 30.

The ring member 34 comprises a platinum-iridium alloy coated with an iridium oxide, or any other suitable combination of materials. The fixation member 42 comprises a metal or metal alloy such as Nitinol or an MP35N alloy, or any other suitable material.

Figure 3:
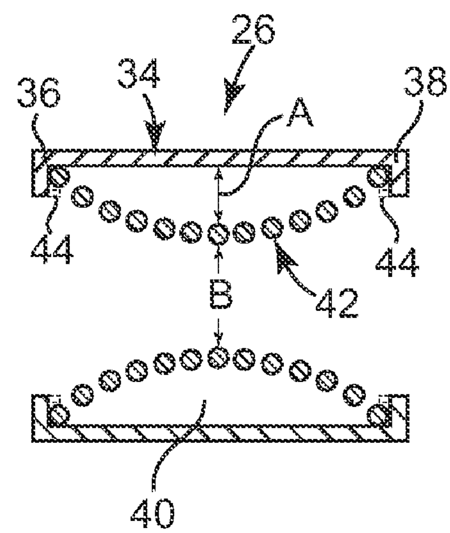
FIG. 3 shows a longitudinal cross-section of a portion of a lead electrode according to some embodiments of the present invention.

As shown in FIG. 2, the fixation member 42 is a captured fixation member that is disposed along the lead shaft 16. In addition, FIG. 3 shows the fixation member 42 prior to the fixation member 42 being placed along the lead shaft 16. In some embodiments, the captured fixation member 42 is predisposed to assume a length longer than the cavity 40. The captured fixation member 42 is placed in longitudinal compression and disposed or captured in the cavity 40 between the flanges 36, 38. In some embodiments, this longitudinal compression causes the captured fixation member 42 to bow inwardly, as shown best in FIG. 3. In some embodiments, the fact that the fixation member 42 is being held in a compressed state by the ring 34 and the flanges 36, 38 provides a friction fit between the fixation member 42 and the ring member 34 and the flanges 36, 38, maintaining the fixation member 42 in the cavity 40. In other embodiments, the flanges 36, 38 have optional tabs 44 (shown in phantom in FIG. 3) to further facilitate maintaining the captured fixation member 42 between the flanges 36, 38.

As shown in FIG. 3, in some embodiments the fixation member 42 has a first configuration in which a medial portion of the fixation member 42 bows radially inwardly away from the inside of the ring 34 a distance "A," forming a space having the dimension "B" within the fixation member 42. In some such embodiments, the fixation member 42 is radially flexible, allowing it to be moved from the first configuration shown in FIG. 3 to a second radially expanded configuration shown in FIG. 2 in which dimension B is increased and distance A is decreased. In some embodiments, when the fixation member 42 is captured within the ring member 34, the fixation member 42 is predisposed to assume the first configuration shown in FIG. 3.

In some embodiments, the conductor member 30 has an outer diameter that is larger than the dimension B shown in FIG. 3. When the electrode 26 is disposed over the conductor member 30, the fixation member 42 is deformed from the first radially constricted configuration shown in FIG. 3 to the second radially expanded configuration shown in FIG. 2 to accommodate the conductor member 30. In some embodiments, because the fixation member 42 is predisposed to assume the first configuration shown in FIG. 3, the fixation member 42 provides a compressive force on the conductor member 30. In some such embodiments, the compressive force from the fixation member 42 causes the conductor member 30 to deform radially inwardly, while in other embodiments the conductor member 30 is sufficiently radially rigid such that the compressive force from the fixation member 42 does not cause a change in dimension of the conductor member 30.

In some embodiments, and as shown in FIG. 2, the unsupported conductor member 30 is sufficiently radially rigid to maintain an open lumen 31 when being compressed by the fixation member 42. For example, the conductor member 30 is not deformed at all by the fixation member 42 as shown in FIG. 2, or the conductor member 30 is deformed but the lumen 31 remains open through the fixation member 42.

In other embodiments, the conductor member 30 has a support member (not show) that radially supports the conductor member 30 in order to maintain an open lumen 31 when the conductor member 30 is being compressed by the fixation member 42. For example, an inner support member is disposed within the conductor member 30 along the entire length of the conductor member 30 or just within the conductor member 30 adjacent the fixation member 42. In other embodiments, the conductor member 30 is supported by other structures along the entire length of the conductor member 30 or just within the conductor member 30 adjacent the fixation member 42. For example, a support member is wound within the coil structure of the conductor member 30, a structural material is formed between or around the filars of the conductor member 30, or the conductor member 30 is otherwise embedded in a structural material (e.g., a polymer).

As shown in FIG. 2, in the second configuration a space remains between the inner surface of the ring 34 and the captured fixation member 42. In other embodiments, when in the second configuration, the captured fixation member 42 is disposed flush with the inner surface of the ring 34 (the dimension A is zero, or essentially zero).

In some embodiments a portion of the fixation member 42 forms a first helical pattern and a portion of the conductor member 30 forms a second helical pattern. For example, as shown in FIG. 2, both the fixation member 42 and the conductor member 30 comprise helical coils. In some embodiments, the fixation member 42 and/or the conductor member 30 are helically wound generally around and along the axis of the lead body. In some embodiments, the direction and pitch of the first and second helical patterns are the same, or substantially the same, allowing the fixation member 42 to essentially be threaded on to the conductor member 30. The interaction between the two helical patterns facilitates the formation of an interference fit between the conductor member 30 and the fixation member 42.

In other embodiments, the direction of the pitch of the first and second helical patterns is the same, but the pitch of the helical pattern of the fixation member 42 is smaller or larger than the pitch of the conductor member 30 (e.g., 0.8, 0.9, 1.1 or 1.2 times the pitch of the helical pattern of the conductor member 30). The difference in pitch causes the fixation member 42 and/or the conductor member 30 to be longitudinally compressed or stretched, further facilitating an interference fit therebetween.

Figure 4:
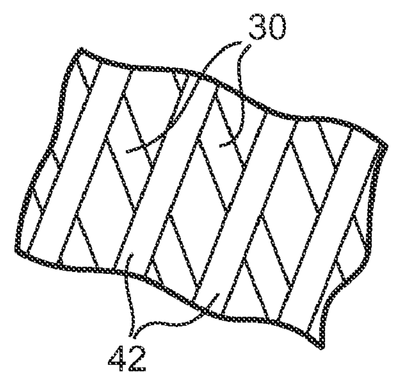
FIG. 4 shows an enlarged view of a fixation member disposed along a coiled portion of a medical lead according to some embodiments of the present invention.

In yet other embodiments, the direction of the helical pattern of the fixation member 42 is opposite the helical pattern of the conductor member 30. For example, FIG. 4 shows an enlarged view of the windings of the fixation member 42 disposed over the windings of the conductor member 30 where the helical pattern of the fixation member 42 has an opposite direction relative to the helical pattern of the conductor member 30. In some embodiments, the opposite direction of these helical patterns facilitates a reduced contact area between the fixation member 42 and the conductor member 30 compared to embodiments in which the helical patterns have the same direction. This relatively smaller area of interaction between the fixation member 42 and the conductor member 30 provides for increased force per unit area between the fixation member 42 and the conductor member 30.

In some embodiments, the different types of interference fit provided by the interaction between the helical patterns of the fixation member 42 and the conductor member 30 is in addition to the interference fit provided by the compressive force exerted by the fixation member 42. In other embodiments, the fixation member 42 exerts little or no compressive force on the conductor member 30 and an interference fit is provided by the mechanical interaction between the first and second helical patterns (e.g., the helical patterns are threaded onto one another).

Figure 5:
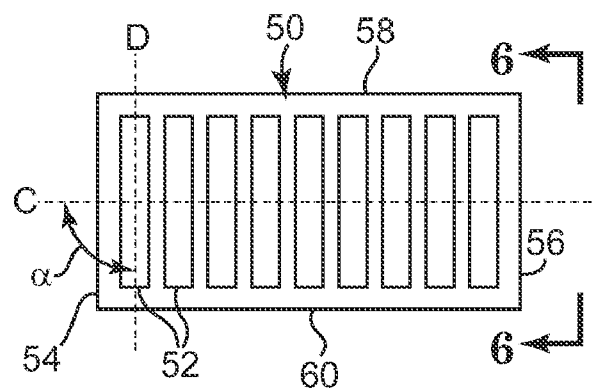
FIG. 5 shows a fixation member in a flat configuration according to some embodiments of the present invention.

FIG. 5 shows a fixation member 50 in a flat configuration according to some embodiments of the present invention. The fixation member 50 defines a number of openings 52 and has a longitudinal axis "C," ends 54, 56 and sides 58, 60. The openings 52 are formed across the width of the fixation member 50 and are substantially parallel with one another. In some embodiments, the openings 52 are formed along, or parallel to, an axis "D," which extends at a right angle a to the longitudinal axis C.

Figure 6:
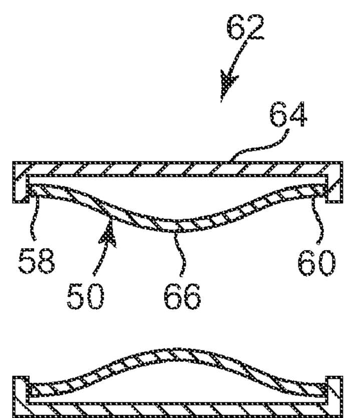
FIG. 6 shows a longitudinal cross-section of an electrode according to some embodiments of the present invention.

FIG. 6 shows a longitudinal cross-section of an electrode 62 according to some embodiments of the present invention. The ends 54, 56 of the fixation member 50 are brought together to form a slotted tube, which, as shown in FIG. 6, is disposed inside the ring member 64. The ring member 64 is similar to any of the ring members described above with respect to FIGS. 2 and 3. Because the ends 54, 56 of the fixation member 50 are longer than the cavity formed by the ring member 64, the medial portion 66 of the fixation member 50 bows radially inward, similar to the fixation member 42 discussed above. In some embodiments the inner dimension of this medial portion 66 is smaller than the outer dimension of the conductor member 30, and fixation member 50 provides a compressive force on the conductor member 30, similar to the fixation member 42 discussed above.

The fixation member 50 comprises a sheet of metal or metal alloy such as Nitinol or any other suitable material. The openings 52 are removed from the sheet using LASER etching, EDM, grinding, or any other suitable method. With the openings 52 formed at a right angle a to the longitudinal axis C as shown in FIG. 5, when the electrode 26 is disposed on the conductor member 30, the openings 52 extend along the length of the lead shaft 16.

Figure 7:
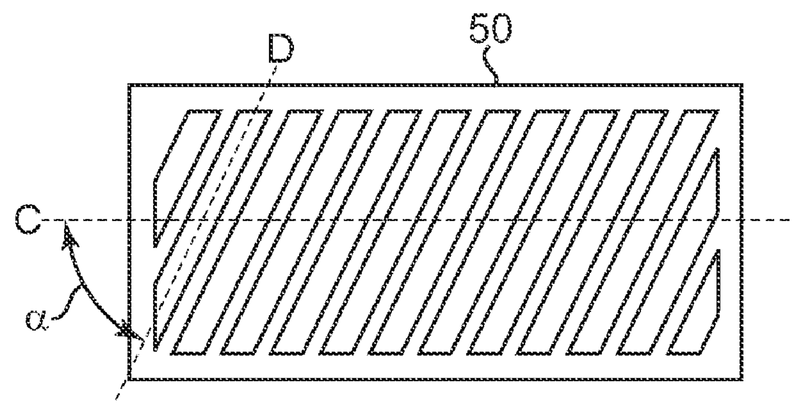
FIG. 7 shows a fixation member in a flat configuration according to some embodiments of the present invention.

In other embodiments, the openings 52 are formed at other angles with respect to the longitudinal axis C. For example, FIG. 7 shows the fixation member 50 in a flat configuration according to some embodiments of the present invention. As shown, the angle a between the axes C and D is smaller than 90 degrees. When the sheet of material is formed into a tubular member and placed within the ring electrode 34, the openings 52 form a helical pattern. In some embodiments, this helical pattern is formed in the same direction as a helical pattern of the conductor member 30. In some such embodiments, the pitch of the helical pattern formed by the openings 52 is matched to or is greater or lesser than the pitch of a helical pattern of the conductor member 30, similar to the helical patterns discussed above with respect to FIGS. 2 and 3. In other embodiments, the helical pattern formed by the openings 52 is formed in a direction opposite a helical pattern of the conductor member 30, similar to the helical patterns discussed above with respect to FIG. 4.

As mentioned above, in some embodiments the fixation member 42, 50 can be threaded onto the conductor member 30. In other embodiments, the fixation member 42, 50 is advanced axially over the conductor member 30 with little or no rotational movement. In some embodiments, the electrode 26, 62 is disposed over the conductor member 30 prior to placing the insulative member 32 on the conductor member 30. Once the electrode 26, 62 is in place, the insulative member 32 is disposed over the conductor member 30 proximal and distal of the electrode 26, 62, as shown in FIG. 2. The insulative member 32 is disposed over the conductor member 30 using any suitable method, for example insert molding, dip coating, passing the electrode/conductor member assembly through an extrusion system and extruding the insulative member 32 on the conductor member 30, or by heat shrinking a tubular insulative member 32 around the conductor member 30.

In addition to, or in place of, the insulative member 32, an insulation layer is optionally formed over the conductor member 30 prior to disposing the electrodes 26, 62 along the conductor member 30. For example, in embodiments in which the conductor member 30 is a coil conductor, the one or more filars in the coil conductor are individually provided with an insulative coating. In other embodiments, the conductor member 30 has an insulation layer disposed over the outer surface of the conductor member 30 prior to the electrode 26, 62 being disposed on the conductor member 30. The electrode 26, 62 is disposed over the insulation material, and the fixation member 42, 50 forms an interference fit with the insulation material. The fixation member 42, 50 is then heated, causing the insulation material to be softened. The heated insulation material flows, allowing the fixation member 42, 50 to form an interference fit with a conductive portion of the conductor member 30.

In other embodiments, the fixation member 42, 50 comprises a one-way shape memory material, for example a one-way shape memory alloy such as Nitinol. The fixation member 42, 50 has an original shape that is shaped and configured to form an interference fit with the conductor member 30. For example, the original shape provides an inner dimension B that is smaller than an outer dimension of the conductor member 30, as best shown in FIG. 3. The fixation member 42, 50 is then deformed such that it is easily disposed over the conductor member 30. For example, the fixation member 42, 50 is deformed so that inner dimension B is about the same as, or larger than, an outer dimension of the conductor member 30. Once the electrode 26, 62 is in place, the fixation member 42, 50 is heated to raise its temperature above its austenite start ($A_s$) temperature and, in some embodiments, above its austenite finish ($A_f$) temperature. This causes the fixation member 42, 50 to revert back to its original shape, providing an interference fit with the conductor member 30.

Figure 8:
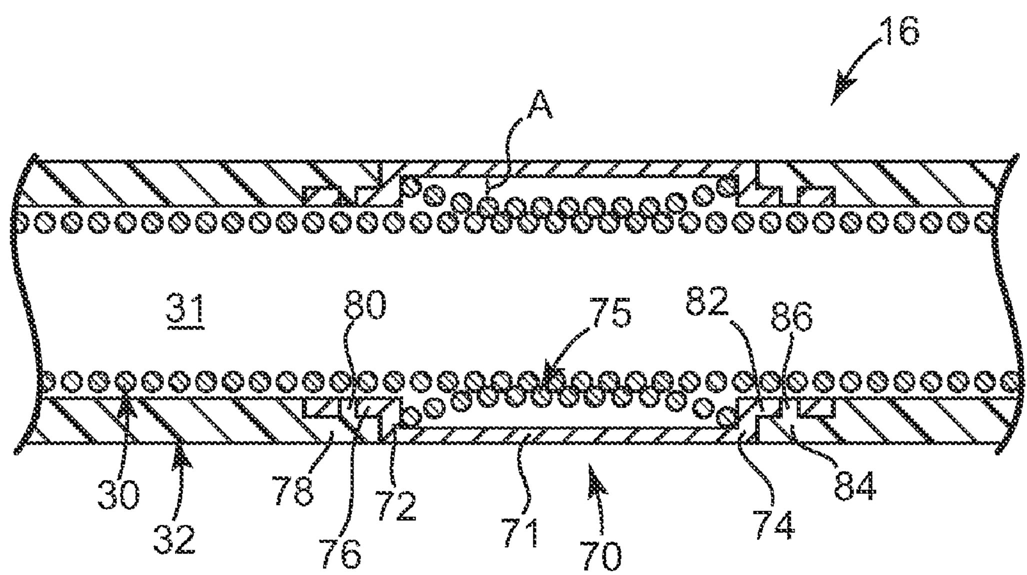
FIG. 8 shows a longitudinal cross-section of a portion of a medical lead according to some embodiments of the present invention.

FIG. 8 shows a longitudinal cross-section of a portion of the shaft 16 according to some embodiments of the present invention. The lead shaft 16 is similar to the lead structure shown in FIG. 2 with an alternate ring member 71. An electrode 70 includes a ring member 71 with a proximal flange 72 and a distal flange 74, and a fixation member 75 disposed within the ring member 71. The fixation member 75 is shown as a captured coil, but can also be similar to any of the fixation members discussed above. The proximal flange 72 has a proximal flange extension 76, and a portion 78 of the insulative member 32 is formed over the proximal flange extension 76. The proximal flange extension 76 optionally has a hole or opening 80 formed therein and a portion of the insulative member 32 can extend into the hole or opening 80, forming a connection between the insulative member 32 and the proximal flange extension 76. Similarly, the distal flange 74 has a distal flange extension 82. A portion 84 of the insulative member 32 is disposed over the distal flange extension 82. The distal flange extension 82 also optionally has a hole or opening 86 formed therein, and the insulative member 32 extends into this hole or opening 86, forming a connection between the insulative member 32 and the distal flange extension 82.

The insulative member 32 is attached to the proximal and distal flange extensions 76, 82 using any suitable method, for example by heat shrinking, extrusion, dip coating, insert molding, or the insulative member 32 can be adhered to the proximal and distal flange extensions 76, 82 using an adhesive.

Figure 9A:
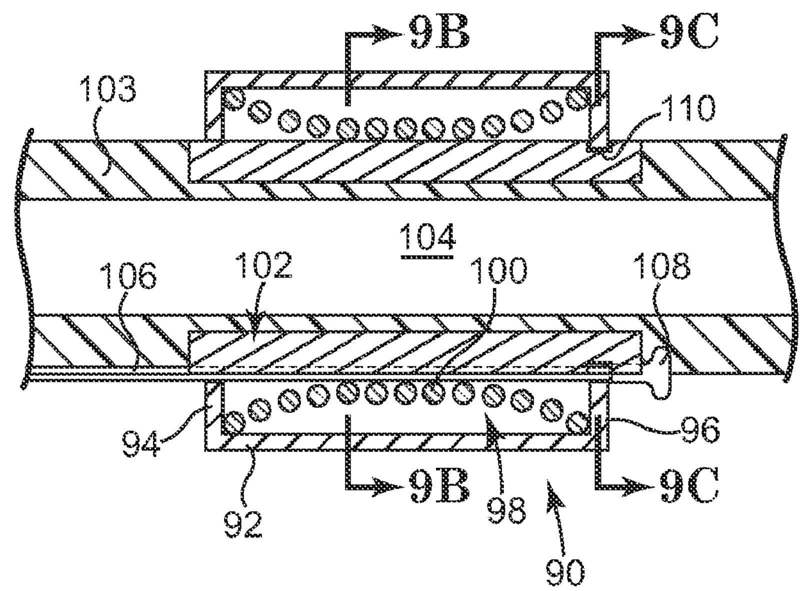
FIG. 9A shows a longitudinal cross-section of a portion of a medical lead according to some embodiments of the present invention.

FIG. 9A shows a longitudinal cross-section of a portion of a medical lead according to some embodiments of the present invention. The electrode 90 has a ring member 92 with a proximal flange 94 and a distal flange 96. The ring member 92 and the proximal and distal flanges 94, 96 define a cavity 98. Disposed in the cavity 98 is a fixation member 100, which is shown as a captured coil fixation member, but can be any of the fixation members described herein. The shaft of the medical lead has an inner support member 102 that is embedded in a portion of a lead body 103. The lead body 103 defines a lumen 104. A conductor member 106 extends longitudinally through a wall of the lead body 103 and through a wall of the inner support member 102.

Figure 9B:
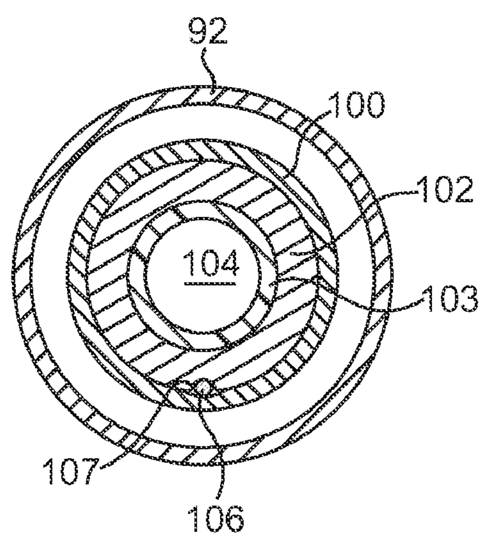
FIGS. 9B and 9C show cross-sections of the medical lead shown in FIG. 9A.

FIG. 9B shows a cross-section of the lead of FIG. 9A. The conductor member 106 is disposed partially within a first channel 107 of the inner support member 102, and a portion of the conductor member 106 extends radially out from an outer surface of the inner support member 102. For example 40% or less, 25% or less, or 10% or less of the diameter of the conductor member 106 extends radially out from the outer surface of the inner support member 102. Further, a distal crimp tube 108 (see FIG. 9A) is crimped onto a distal portion of the conductor member 106. The distal crimp tube 108 forms an enlargement on the distal end of the conductor member 106, which prevents the conductor member 106 from being pulled proximally through the first channel 107.

When the fixation member 100 is disposed over the inner support member 102, the fixation member 100 contacts the portion of the conductor member 106 that extends radially out from the outer surface of the inner support member 102, forming an electrical connection between the fixation member 100 and the conductor member 106. In some embodiments, the lead comprises multiple conductor members 106 extending through multiple channels 107 and the fixation member 100 contacts one or more of the multiple conductor members 106.

In some embodiments, the fixation member 100 provides a compressive force on the conductor member 106 and the inner support member 102. The inner support member 102 is sufficiently radially rigid in order to prevent the inner support member 102 from being radially deformed by the fixation member 100. In such embodiments, the conductor member 106 is compressed between the inner support member 102 and the fixation member 100, providing for secure electrical contact between the fixation member 100 and the conductor member 106.

Figure 9C:
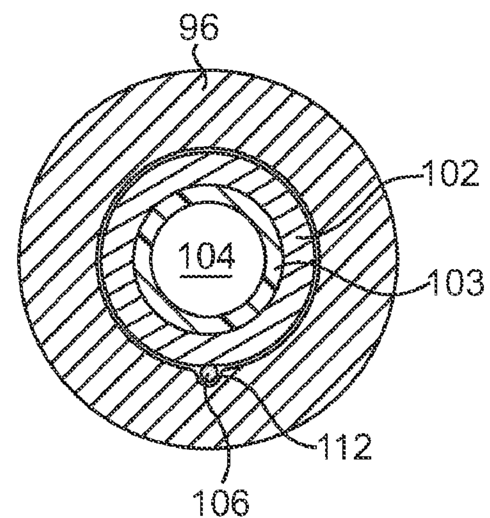

Referring again to FIG. 9A, the inner support member 102 also has a snap fit groove 110. In some embodiments, the distal flange 96 has an inner diameter that is smaller than the outer diameter of the inner support member 102, but the distal flange 96 is sufficiently radially flexible such that the distal flange 96 can be expanded to fit around the inner support member 102. As the ring member 92 (and the flange 96) is being advanced distally over the inner support member 102, the flange 96 is in this expanded configuration. When the flange 96 reaches the snap fit groove 110, the flange 96 snaps into the reduced outer diameter portion of the snap fit groove 110, longitudinally fixing the ring member 92 along the inner support member 102. In addition, as shown in FIG. 9C, a portion of the flange 96 also has a channel 112 formed therein in order to accommodate the conductor member 106 as the flange 96 is being advanced over the inner support member 102.

In some embodiments, and as shown in FIG. 9A, the inner support member 106 is embedded within the lead body 103. In other embodiments, the inner support member 102 is disposed over the top of the lead body 103. In yet other embodiments, the inner support member 102 is a portion of the lead body 103, for example where the lead body 103 comprises a relatively rigid polymeric material such as PEEK. In some such embodiments, the channel 107 is formed in the lead body 103, and the conductor member 106 is disposed therein. In yet other embodiments, the channel 107 is formed in the lead body 103 and the inner support member 102 is disposed within a lumen of the lead body 103. Further, in order to provide a continuous outer dimension along the lead, after the electrode 90 is disposed over the inner support member 102, an outer layer of material is optionally disposed around the lead body 103 distal and proximal of the electrode 90. In some embodiments, this outer layer of material has a thickness such that the outer surface of the lead will be flush with the outer surface of the electrode 90.

Figure 10A:
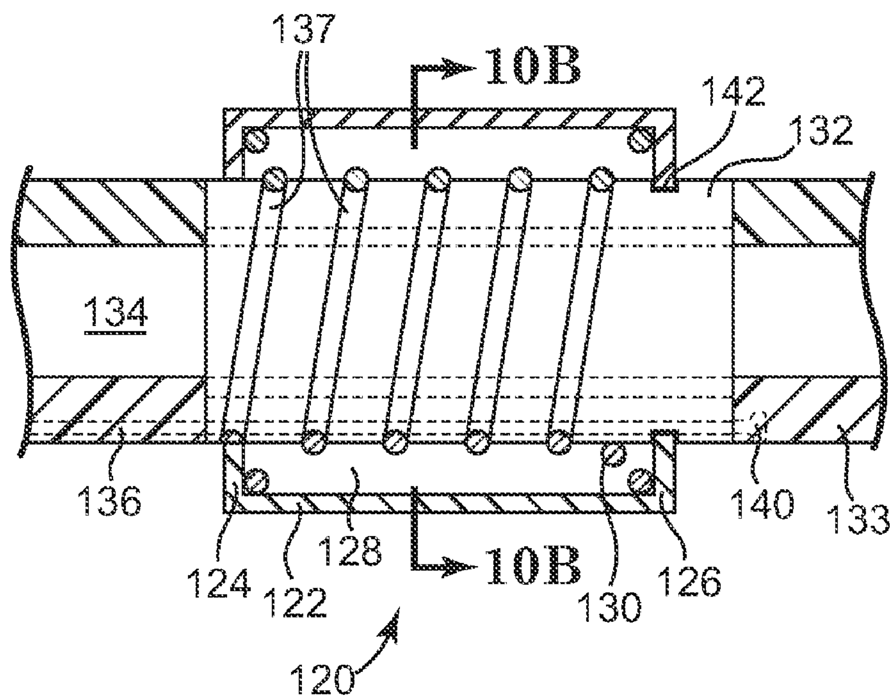
FIG. 10A shows a longitudinal cross-section of a portion of a medical lead according to some embodiments of the present invention.
Figure 10B:
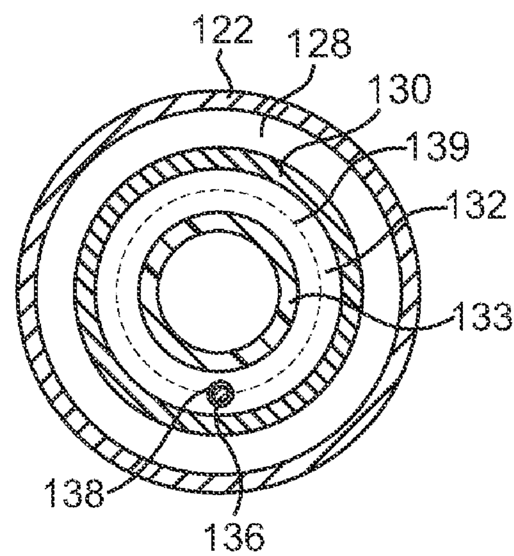
FIG. 10B shows a cross-section of the medical lead shown in FIG. 10A.

FIG. 10A shows a longitudinal cross section of a portion of a lead according to some embodiments of the present invention and FIG. 10B shows a cross section of the lead shown in FIG. 10A. The lead shown in these figures includes an electrode 120. The electrode 120 has a ring member 122, which has a proximal flange 124 and a distal flange 126. The ring member 122 and the proximal and distal flanges 124, 126 define a cavity 128. The electrode 120 further comprises a fixation member 130 that is disposed in the cavity 128. The fixation member 130 is shown as a captured coil fixation member, but can be any of the fixation members described herein.

The lead also has an inner support member 132 and a lead body 133. The inner support member 132 is embedded within the lead body 133, and the lead body 133 defines a lumen 134. The inner support member 132 has a conductor member 136 extending longitudinally through a channel 138 (shown in FIG. 10B) in a wall of the inner support member 132.

The inner support member 132 has a number of threads 137 formed in an outer surface thereof. As shown best in FIG. 10B, the threads 137 have a depth (the depth is indicated by dashed line 139), and the threads 137 are sufficiently deep to expose portions of the conductor member 136. The fixation member 130 comprises portions (e.g., individual windings of the fixation member 130) that are sized and shaped to extend into the threads 137 and contact the conductor member 136. For example, as shown best in FIG. 10A, the threads 137 and the individual windings of the fixation member 130 both have similar cross-sectional shapes. The individual windings of the fixation member 130 are sized to extend into the threads 137 to a depth sufficient to contact the conductor member 136.

In some embodiments, the fixation member 130 and the threads 137 have the same pitch. In other embodiments, the fixation member 130 and the threads 137 have different pitches, causing the fixation member to become either longitudinally stretched or longitudinally compressed when threaded onto the threads 137. This longitudinal stretching or compression facilitates the fixation of the fixation member 130 (and the ring 122 in which the fixation member 130 is captured) to the inner support member 132, similar to other embodiments of the fixation member described above.

In addition, in some embodiments the fixation member 130 exerts a radial compressive force on the inner support member 132, similar to other embodiments of the fixation member described above. The inner support member 132 is sufficiently radially rigid in order to prevent the inner support member 132 from being radially compressed by the fixation member 130. In such embodiments, the conductor member 136 is compressed between the inner support member 132 and the fixation member 130, providing secure electrical contact between the fixation member 130 and the conductor member 136.

A distal crimp tube 140 is crimped onto a distal portion of the conductor member 136. The distal crimp tube 140 forms an enlargement on the distal end of the conductor member 136, which prevents the conductor member 136 from being pulled proximally through the first channel 138.

The inner support member 132 also has a snap fit groove 142. In some embodiments, the distal flange 126 has an inner diameter that is smaller than the outer diameter of the inner support member 132 and the distal flange 126 is sufficiently radially flexible such that the distal flange 126 can be expanded to fit around the inner support member 132. As the ring member 92 (and the flange 96) is being advanced distally over the inner support member 132, the flange 126 is in this expanded configuration. When the flange 126 reaches the snap fit groove 142, the flange 126 snaps into the reduced outer diameter portion of the snap fit groove 142, longitudinally fixing the ring member 126 along the inner support member 132. In some embodiments, the snap fit groove 142 is sufficiently shallow such that the conductor member 136 is not exposed in the snap fit groove 142.

In some embodiments, as shown in FIG. 10A, the inner support member 132 is embedded within the lead body 133. In other embodiments, the inner support member 132 is disposed over the top of the lead body 133. In yet other embodiments, the inner support member 132 is a portion of the lead body 133, for example where the lead body 133 comprises a relatively rigid polymeric material such as PEEK. In some such embodiments, the channel 138 is formed in the lead body 133, and the conductor member 136 is disposed therein. In yet other embodiments, the channel 138 is formed in the lead body 133 and the inner support member 132 is disposed within a lumen 134 of the lead body 133, providing radial support for the fixation member 130.

Further, in order to provide a continuous outer surface along the lead, after the electrode 120 is disposed over the inner support member 132, an outer layer of material is optionally disposed around the lead body 133 distal and proximal of the electrode 120. In some embodiments, this outer layer of material has a thickness such that the outer surface of the lead will be flush with the outer surface of the electrode 120.

In addition, in some embodiments the electrodes discussed above have an outer surface that is treated. For example, the outer surface has a coating disposed thereon and/or the outer surface is conditioned. In some embodiments, the outer surface of the electrode is coated with one or more of a drug, iridium oxide (IROX), titanium nitride, and/or platinum black. In addition to, or in place of, the one or more coatings, in some embodiments the outer surface is conditioned, for example to provide a textured (e.g., porous or textured) surface. The coatings and/or the surface conditioning may provide an outer surface that reduces thresholds and/or facilitates tissue integration and/or provides a therapeutic treatment for the patient.

Many such coatings and surface conditionings are easily damaged by heat or mechanical force, for example heat or mechanical force used when fixing the electrode at a location along a lead body. In some embodiments, the structures and methods described herein facilitate the fixation of the electrode at a location along a lead body without the use of either heat (e.g., without welding) or a mechanical force being imparted on the outer surface of the electrode (e.g., without crimping or staking the electrode to the lead). In some such embodiments, avoiding the use of such heat or mechanical bonding facilitates the preservation of the coating or surface conditioning on the outer surface of the electrode.

Figure 11:
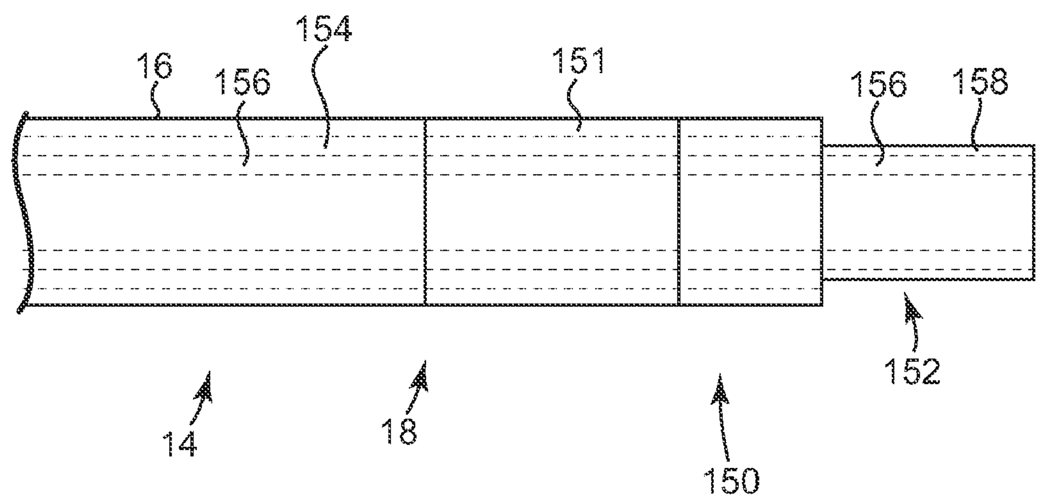
FIG. 11 shows a proximal connector of a medical lead.

FIG. 11 shows a proximal connector 150 of a medical lead 14. The proximal connector 150 is disposed in the medical lead proximal portion 18 and comprises a terminal ring 151 and a terminal pin 152. In some embodiments, the terminal ring 151 is similar in construction to any of the electrodes described herein. The portion of the lead 14 along which the terminal ring 151 is disposed has a first conductor member 154 (shown in phantom in FIG. 11), which in some embodiments is a proximal portion of any of the conductor members discussed herein or an extension thereof. An optional second conductor member 156 (also shown in phantom in FIG. 11) also extends along the lead shaft 16, for example within the first conductor 154. The second conductor member 156 can be similar to any of the conductor members discussed herein. In some embodiments, the second conductor member 156 extends through the terminal ring 151 into the terminal pin 152.

In some embodiments, a fixation member (not shown in FIG. 11) disposed within the terminal ring 151 forms an interference fit with the first conductor 154, for example as discussed with respect to any of the fixation members and conductors described herein. In some embodiments, the terminal pin 152 includes a ring member 158 that has a fixation member (not shown in FIG. 11) that forms an interference fit with the optional second conductor 156, for example as discussed with respect to any of the fixation members and conductors described herein. Further, the proximal connector 150 is shaped and configured to be connected to the pulse generator 12 (as shown in FIG. 1) or other controller for the system.

While many of the embodiments discussed herein are described with respect to cardiac leads and/or cardiac procedures, those of ordinary skill in the art would recognize that any of the structures shown and described herein are also suitable for other types of medical leads, for example neurological leads.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical lead comprising:

an elongate lead body including a conductor extending from a proximal portion of the lead body to a distal portion of the lead body;

a fixation member; and an electrode disposed along the conductor and including an outer electrically active surface, the electrode defining an inner cavity with the fixation member disposed therein; and wherein the fixation member is captured within the cavity and the fixation member exerts a compressive force on the conductor, mechanically and electrically connecting the conductor to the fixation member and the electrode.

2. The medical lead of claim 1, wherein the fixation member has a first helical pattern, the conductor has a second helical pattern, and the first and second helical patterns are formed in the same helical direction.

3. The medical lead of claim 1, wherein the fixation member has a first helical pattern, the conductor has a second helical pattern, and the first and second helical patterns are formed in opposite helical directions.

4. The medical lead of claim 1, wherein the fixation member comprises a captured coil.

5. The medical lead of claim 1, wherein the fixation member comprises a slotted tubular member.

6. A medical lead comprising:

an elongate shaft including a conductor extending from a proximal portion of the shaft to a distal portion of the shaft; and an electrode disposed along the shaft, the electrode including a ring member and a fixation member captured within the ring member;

wherein the fixation member exerts a compressive force on the conductor, thereby forming an interference fit and an electrical connection between the fixation member and conductor member.

7. The medical lead of claim 6, wherein the fixation member has a first helical pattern, the conductor has a second helical pattern, and the first and second helical patterns are formed in the same helical direction.

8. The medical lead of claim 7, wherein the fixation member has a first helical pattern, the conductor has a second helical pattern, and the first and second helical patterns are formed in opposite helical directions.

9. The medical lead of claim 6, wherein the conductor member comprises a cable or wire.

10. The medical lead of claim 9, wherein the elongate shaft further comprises a tubular support member with a channel formed therein and wherein the cable or wire extends longitudinally through the channel, wherein at least a portion of the cable or wire is exposed along an outer surface of the support member, and wherein the fixation member forms an interference fit with both the support member and the exposed portion of the cable or wire.

11. The medical lead of claim 10, wherein the support member has one or more threads defined in an outer surface thereof, wherein the cable or wire is exposed within the one or more threads and wherein the fixation member forms an interference fit with both the support member and the exposed portion of the cable or wire.

12. A method of making a medical lead comprising:

providing a conductor;

providing an electrode having a ring member and a fixation member disposed within the ring member, the fixation member sized and configured to form an interference fit with the conductor;

disposing the electrode over a portion of the conductor, forming an interference fit between the fixation member and the conductor; and disposing an insulative material over the conductor distal and proximal of the electrode.

13. The method of claim 12, wherein the conductor is a helically wound conductor having a first helical pattern and the fixation member defines a second helical pattern and wherein the first and second helical patterns have the same helical direction.

14. The method of claim 13, wherein disposing the electrode over a portion of the conductor comprises threading the fixation member over the conductor.

15. The method of claim 12, wherein the conductor is a helically wound conductor having a first helical pattern and the fixation member defines a second helical pattern, the first and second helical patterns have opposite helical directions and disposing the electrode over a portion of the conductor comprises sliding the fixation member longitudinally over the conductor.

16. The method of claim 12, wherein an outer surface of the conductor is insulated and, after the electrode is disposed over a portion of the conductor, the fixation member is heated and melts through the insulation material on the outer surface of the conductor, making electrical contact with the conductor.

17. The method of claim 12, wherein the fixation member comprises a material with one way shape memory having an austenite start temperature and an austenite finish temperature, the method further including steps of:

disposing the electrode over a portion of the coil conductor when the fixation member is in a martensite state and is in a radially expanded configuration;

raising the temperature of the fixation member above the austenite start temperature;

causing the fixation member to move from a radially expanded configuration to a radially constricted configuration; and forming an interference fit between the fixation member and the conductor.

18. The method of claim 17, wherein the fixation member is raised above the austenite finish temperature.

19. The method of claim 12, wherein the fixation member has a first, radially constricted configuration and a second, radially expanded configuration, wherein the fixation member is predisposed to assume the first configuration; and wherein the inner diameter of the fixation member in the first configuration is smaller than the outer diameter of the conductor such that placing the fixation member on the conductor causes the fixation member to move from the first to the second configuration and exert compressive force on the conductor.

20. The method of claim 12, wherein the insulative material is disposed over the conductor after the electrode is disposed over the conductor.

* * * * *